(12) United States Patent
Jung (10) Patent No.: US 10,568,592 B2
(45) Date of Patent: Feb. 25, 2020

(54) X-RAY MODULE ASSEMBLY FOR PORTABLE X-RAY DEVICE

(71) Applicant: ELIM ELECTRONICS CORPORATION, Cheonan-shi (KR)

(72) Inventor: Jae Duck Jung, Cheonan-shi (KR)

(73) Assignees: ELIM ELECTRONICS CORPORATION, Cheonan-shi, ChungCheongnamdo (KR); Jae Duck Jung, Cheonan-shi, ChungCheongnamdo (KR)

( * ) Notice: Subject to any disclaimer, the term of this patent is extended or adjusted under 35 U.S.C. 154(b) by 241 days.

(21) Appl. No.: 15/787,164

(22) Filed: Oct. 18, 2017

(65) Prior Publication Data
US 2018/0140263 A1 May 24, 2018

(30) Foreign Application Priority Data

Nov. 23, 2016 (KR) ........................ 10-2016-0156276

(51) Int. Cl.
*A61B 6/14* (2006.01)
*A61B 6/00* (2006.01)
(Continued)

(52) U.S. Cl.
CPC ............ *A61B 6/145* (2013.01); *A61B 6/4405* (2013.01); *H01J 35/00* (2013.01); *H05G 1/02* (2013.01)

(58) Field of Classification Search
CPC .... A61B 6/145; A61B 6/4405; H01J 2235/00; H01J 2235/16; H01J 35/00; H01J 35/02;
(Continued)

(56) References Cited

U.S. PATENT DOCUMENTS 4,418,421 A * 11/1983 Kitadate .................. H05G 1/06
378/102
4,646,338 A * 2/1987 Skillicorn ............... H01J 35/04
378/110
(Continued)

FOREIGN PATENT DOCUMENTS

KR   1020050090667   9/2005
KR   1020080005000   1/2008
(Continued)

OTHER PUBLICATIONS

Korean Office Action—Korean Application No. 10-2016-0156276 dated Sep. 13, 2017, citing KR 101427555, KR 1020050090667, KR 1020080005000, KR 1020150031395 and KR 101684400.

*Primary Examiner* — David P Porta
*Assistant Examiner* — Djura Malevic
(74) *Attorney, Agent, or Firm* — Novick, Kim & Lee, PLLC; Jae Youn Kim (57) ABSTRACT

Provided is an X-ray module assembly for a portable X-ray device, in which an X-ray tube is made of a carbon nano tube or a filament-type tube, preferably, a carbon nano tube, high-voltage capacitors and high-voltage diodes are arranged space-intensively, fine control of X-ray emission may be achieved by molding the above-configured X-ray module within a case having a reduced size and a reduced weight with thermosetting resin, preferably, epoxy-based resin, more preferably, soft epoxy-based resin, so that radiation exposure to a user may be minimized, power consumption may be greatly reduced, the X-ray module assembly may be downsized and lightened, an insulation effect is excellent, and the X-ray module assembly may be used semi-permanently. The X-ray module for a portable X-ray device includes an X-ray tube, a high-voltage transformer structure, a plurality of high-voltage capacitors, and a plu-
(Continued)

rality of high-voltage diodes, and is fixedly supported by a tube guide.

12 Claims, 7 Drawing Sheets (51) Int. Cl.
*H01J 35/00* (2006.01)
*H05G 1/02* (2006.01)

(58) Field of Classification Search
CPC .. H01J 35/32; H05G 1/02; H05G 1/04; H05G 1/06
See application file for complete search history.

(56) References Cited

U.S. PATENT DOCUMENTS

| | | | | | |
|---|---|---|---|---|---|
| 4,694,480 | A * | 9/1987 | Skillicorn | ............... | H01J 35/12 378/102 |
| 4,920,554 | A * | 4/1990 | Gabbay | ................... | H01J 35/16 378/200 |
| 5,077,771 | A * | 12/1991 | Skillicorn | ............... | H01J 35/16 378/102 |
| 5,111,493 | A * | 5/1992 | Siedband | ................ | H01J 35/16 378/102 |
| 5,442,677 | A * | 8/1995 | Golden | .................... | H05G 1/06 378/101 |
| 5,517,545 | A * | 5/1996 | Nakamura | ................ | H05G 1/06 378/101 |
| 6,038,287 | A * | 3/2000 | Miles | ........................ | A61B 6/14 378/117 |
| 6,169,782 | B1 * | 1/2001 | Zetterlund | ............... | H05G 1/12 378/101 |
| 6,205,200 | B1 * | 3/2001 | Boyer | ....................... | H05G 1/06 378/101 |
| 6,619,842 | B1 * | 9/2003 | Artig | ....................... | H01J 35/10 378/140 |
| 6,775,353 | B2 * | 8/2004 | Thandiackal | ........... | H01J 35/16 378/119 |
| 7,077,567 | B1 * | 7/2006 | Molteni | ................... | H05G 1/06 378/193 |
| 7,254,216 | B2 * | 8/2007 | Thandiackal | .......... | A61B 6/032 378/157 |
| 7,496,178 | B2 * | 2/2009 | Turner | ................. | A61B 6/4405 378/101 |
| 9,480,135 | B2 * | 10/2016 | Kwon | .................... | H01J 35/025 |
| 2003/0081730 | A1 * | 5/2003 | Thandiackal | ........... | H01J 35/16 378/121 |
| 2005/0053199 | A1 * | 3/2005 | Miles | ...................... | A61B 6/145 378/197 |
| 2006/0098778 | A1 * | 5/2006 | Oettinger | ................. | H05G 1/06 378/101 |
| 2010/0310053 | A1 * | 12/2010 | Yamamoto | ............ | H01J 35/025 378/200 |
| 2012/0027179 | A1 * | 2/2012 | Ogata | .................... | H01J 35/045 378/101 |
| 2013/0129051 | A1 * | 5/2013 | Nakano | ................. | G01N 23/207 378/71 |
| 2014/0211923 | A1 * | 7/2014 | Chen | ....................... | H05G 1/025 378/105 |
| 2014/0270083 | A1 * | 9/2014 | Dinsmore | ............... | H01J 35/16 378/109 |
| 2016/0073485 | A1 * | 3/2016 | Kwan | .................... | H01J 35/025 378/104 |
| 2017/0251545 | A1 * | 8/2017 | Klinkowstein | ......... | H01J 35/06 |
| 2019/0059834 | A1 * | 2/2019 | Chang | ..................... | A61B 6/14 |

FOREIGN PATENT DOCUMENTS

| | | |
|---|---|---|
| KR | 101427555 | 8/2014 |
| KR | 1020150031395 | 3/2015 |
| KR | 101684400 | 12/2016 |

* cited by examiner

X-RAY MODULE ASSEMBLY FOR PORTABLE X-RAY DEVICE

CROSS-REFERENCE TO RELATED APPLICATION

This application claims priority from and the benefit under 35 U.S.C. § 119(a) of Korean Patent Application No. 10-2016-0156276, filed on Nov. 23, 2016, which is hereby incorporated by reference for all purposes as if fully set forth herein.

BACKGROUND OF THE INVENTION

1. Field of the Invention

The present invention relates to an X-ray module assembly for a portable X-ray device, and more particularly, to an X-ray module assembly for a portable X-ray device, in which an X-ray tube, which is a key component of a portable X-ray device, is made of a carbon nano tube or a filament-type tube, preferably, a carbon nano tube, high-voltage capacitors and high-voltage diodes are arranged space-intensively, fine control of X-ray emission may be achieved by molding the above-configured X-ray module within a case having a reduced size and a reduced weight with thermosetting resin, preferably, epoxy-based resin, more preferably, soft epoxy-based resin, so that radiation exposure to a user may be minimized, power consumption may be greatly reduced, the X-ray module assembly may be downsized and lightened, an insulation effect is excellent, and the X-ray module assembly may be used semi-permanently.

2. Description of the Prior Art

In general, a portable X-ray photographing device used in dental clinics was firstly produced for a field operation of an army in U.S. in 1993. In Japan, the portable X-ray photographing device has been used at an emergency time for care of an at-home patient such as a disabled person. In Korean, since 2003, the portable X-ray photographing device has been widely used in dental clinics due to convenience that an operator may take a picture while easily changing a position thereof even in a state in which a patient sits on a medical chair without moving to a shooting room.

In the dental clinic, states of teeth and surrounding tissues should be accurately identified to perform diagnosis and establish a treatment plan. To this end, before a main operation, the states of the teeth and the surrounding tissues are photographed by dental X-ray equipment and are utilized for treatment. The dental X-ray equipment is classified into stand-type (stationary) dental X-ray equipment and portable (mobile) dental X-ray equipment which may be held by an operator and may be operated by hands of the operator. Such portable dental X-ray equipment includes a body configured to irradiate X-rays, a sensor unit configured to obtain an image by the irradiated X-rays, and a monitor unit configured to implement the photographed image.

However, the conventional dental X-ray photographing device has a problem in that because a photographer performs photographing while directly holding the dental X-ray photographing device, scattered radiation generated by a patient as well as leaked radiation generated in a tube head is directly exposed to the photographer. Several studies have reported that exposure dose of the photographer by the dental x-ray photographing device is below the maximum allowable dose per year for radiation workers. However, according to the principles of defense optimization indicating that the radiation exposure should be kept as low as reasonably achievable (ALARA), the photographer should use appropriate radiation protection equipment to reduce radiation exposure.

Further, the dental X-ray photographing device manufactured according to the related art has a problem in that power consumption is high, performance deterioration due to the structure is high, and it is difficult to ensure long life because of severe deformation.

Further, the dental X-ray photographing device manufactured according to the related art is molded by using insulating oil or a silicon-based material to shield X-rays and insulate high voltage. However, it is impossible to permanently use the insulating oil.

Further, the total weight of the dental X-ray photographing device according to the related art is 1,200 g, and the module assembly thereof including the case occupies 50% of the corresponding weight. Therefore, it is difficult to operate the product with one hand due to characteristics of the product, and thus, it is necessary to develop a lighter product.

PRIOR ART DOCUMENT

Patent Document

Korean Patent Application Publication No. 10-2005-0090667 (Application publication date: Sep. 14, 2005)
Korean Patent Application Publication No. 10-2008-0005000 (Application publication date: Jan. 10, 2008)
Korean Patent No. 10-1427555 (Registration date: Jul. 31, 2014)

SUMMARY OF THE INVENTION

An aspect of the present invention is to provide an X-ray module assembly for a portable X-ray device, in which radiation exposure to a user may be minimized, so that stability may be secured, power consumption may be greatly reduced, the X-ray module assembly may be downsized and lightened, an insulation effect is excellent, and the X-ray module assembly may be used semi-permanently.

To solve the above-described technical problems, the present invention may provide an X-ray module assembly for a portable X-ray device, the X-ray module assembly including: an X-ray module including an X-ray tube, a high-voltage transformer structure, a plurality of high-voltage capacitors, and a plurality of high-voltage diodes; and a module case having an open-topped box shape, for embedding the X-ray module therein, wherein the X-ray tube is fixedly supported by a tube guide, the plurality of high-voltage capacitors are arranged between an upper substrate and a lower substrate, and the plurality of high-voltage diodes are arranged on an upper surface of the upper substrate and a lower surface of the lower substrate.

Preferably, the X-ray tube may be a carbon nano tube (CNT) or a filament-type tube.

The tube guide may include a flat upper surface, side walls extending downward from opposite sides of the upper surface, and a lower surface connecting lower portions of the side walls to each other, the upper surface, the side walls, and the lower surface may be formed integrally with each other, and a circular central opening for accommodating the X-ray tube may be defined by the upper surface, the side walls, and the lower surface.

Shoulder parts may protrude upward from boundaries between the upper surface and the side walls in a step shape with respect to the upper surface, first stopping protrusions may protrude upward from upper surfaces of the shoulder parts, and second stopping protrusions may protrude upward from vicinities of boundaries between the upper surface and the shoulder parts on a rear side of the upper surface.

The high-voltage transformer structure may include a high-voltage transformer and a filament transformer which are fixedly arranged on a PCB substrate, a sub PCB may be arranged upright on the PCB substrate at a location that is adjacent to the high-voltage transformer, stopping grooves may be formed through vicinities of opposite edges of the PCB substrate at locations spaced apart from the high-voltage transformer and the filament transformer, a coil connector may be arranged on the sub PCB, and the high-voltage transformer structure may be fixedly supported on the tube guide by inserting and fitting the first stopping protrusions of the tube guide into and with the stopping grooves, when the high-voltage transformer structure is arranged above the tube guide.

A plurality of mounting slots may be formed on the upper substrate and the lower substrate through cutting at regular intervals in accordance with the number of the high-voltage diodes to be mounted, the high-voltage diodes may be arranged above the mounting slots, the high-voltage capacitors may be arranged between the upper substrate and the lower substrate on which the plurality of high-voltage diodes are arranged on an upper surface and a lower surface of the upper substrate and the lower substrate, and the tube guide may be fixedly supported by coupling and attaching the second stopping protrusions of the tube guide to edges of the upper surface of the lower substrate.

When a voltage is 10 kV and soft epoxy is filled, bottom edges of the module case may be chamfered for lightweight such that an insulation distance between a high-voltage side of the X-ray tube and an inner side of the module case is a minimum of 7 to 8 mm.

As described above, according to the present invention, an X-ray tube, which is a key component of a portable X-ray device, is manufactured of a carbon nano tube or a filament-type tube, so that fine control of emission of X-rays may be achieved, and low-dose exposure may be achieved.

Further, a plurality of high-voltage capacitors and a plurality of high-voltage diodes are arranged in a space-intensive manner, and thus, there is no filament, so that power consumption may be greatly reduced.

Further, to lighten a module case having an open-topped box shape for embedding an X-ray module, bottom edges of the module case are chamfered such that an insulation distance between a high voltage side of the X-ray tube and an inner side of the module case is a minimum of 7 mm, and the X-ray module is molded by using thermosetting resin, preferably, epoxy-based resin, more preferably, soft epoxy-based resin. Thus, the X-ray photographing device may be miniaturized and lightened, so that the X-ray photographing device may be conveniently stored, manipulated, and moved. Further, the molding material may be semi-permanently used, an excellent insulating effect is maintained even with the change in a temperature.

BRIEF DESCRIPTION OF THE DRAWINGS

The above and other objects, features and advantages of the present invention will be more apparent from the following detailed description in conjunction with the accompanying drawings, in which.

DETAILED DESCRIPTION OF THE EXEMPLARY EMBODIMENTS

The drawings and a detailed description of the application simply relates to embodiments of the present invention. The advantages and other features of the mechanisms and methods described herein will become clearer to those skilled in the art to which the present invention pertains through a detailed description of the present invention, in which the accompanying drawings illustrating representative embodiments of the present invention are referenced. Otherwise emphasized, the similar or corresponding elements may be denoted by similar or corresponding reference numerals throughout the drawings.

Before a detailed description of at least one embodiment of the present invention, it will be understood that the present invention is not limited to the configurations and arrangements of components described in the specification or illustrated in the drawings in the application. According to the present invention, various embodiments are possible and may be performed and executed in various methods. Further, it may be understood that the grammars and terms employed herein are for description of the present invention and are not intended to limit the present invention.

All comparison expressions used herein, such as the left, the right, the upper, and the lower are described with reference to the accompanying drawing, but are not restrictive terms. It may be understood that the embodiments provide preferred features of variable items of some embodiments, and accordingly, the features, the components, the modules, the elements, and/or aspects may be coupled, interconnected, sequenced, separated, exchanged, located, and/or rearranged without substantially deviating from the disclosed apparatus or method. The shapes or sizes of the components are exemplary, and unless differently explicitly described, may be changed without substantially influencing or restricting the present invention.

Hereinafter, an X-ray module for a portable X-ray device according to an exemplary embodiment of the present invention will be described in detail with reference to the accompanying drawings.

Figure 1:
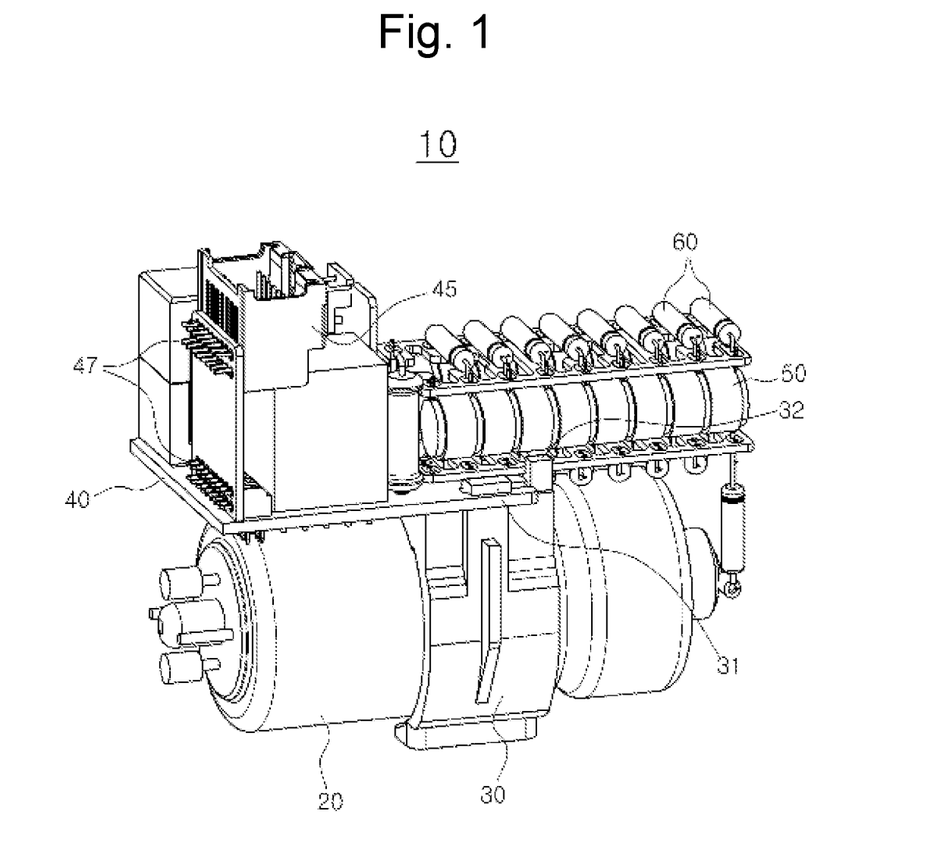
FIG. 1 is a perspective view illustrating an X-ray module for a portable X-ray device according to an exemplary embodiment of the present invention.

An X-ray module for a portable X-ray device according to an exemplary embodiment of the present invention is illustrated in FIG. 1.

Referring to FIG. 1, the X-ray module 10 for a portable X-ray device according to the exemplary embodiment of the present invention mainly includes an X-ray tube 20, a high-voltage transformer structure 40, a plurality of high-voltage capacitors 50, and a plurality of high-voltage diodes 60.

First, the X-ray tube 20, which is a vacuum tube structure having an anode and a cathode or an emitter, is a device in which X-rays are emitted from the anode when a high voltage that is higher than a predetermined voltage is applied and electrons are emitted from a filament or the emitter. That is, the X-ray tube 20 is a device manufactured to make a rapidly moving electron beam to allow the electron beam to collide with a material so as to emit X-rays, According to the present invention, the X-ray tube 20 is made of a carbon nano tube (CNT) to implement low dose exposure through fine control. As widely known, the carbon nano tube is spotlighted as an electric field emission emitter material due to a low threshold electric field and a high electric field emission current density. When the X-ray tube 20 is manufactured of the carbon nano tube, because cold emission not using heat is performed, heating electric power is not required, and the X-ray tube 20 is manufactured in a bipolar tube or a three-pole tube so that emission current may be simply adjusted. Otherwise, the X-ray tube 20 may be manufactured in a filament type tube.

Figure 2:
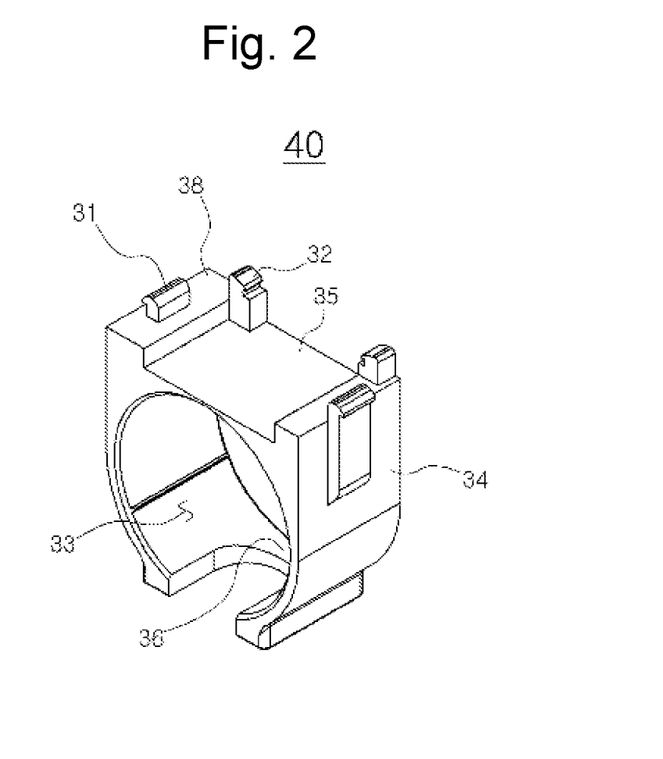
FIG. 2 is an enlarged view illustrating an X-ray tube guide of FIG. 1.

The tube guide 30 for fixedly supporting the X-ray tube 20 is enlargedly illustrated in FIG. 2.

As illustrated in FIG. 2, the tube guide 30 includes a flat upper surface 35, side walls 34 extending downward from opposite sides of the upper surface 35, wherein the side walls 34 firstly extend in a straight line and gradually extends in an arc shape to be converged inward, and a lower surface 36 connecting lower portions of the side walls 34 to each other, wherein a portion of the lower surface 36 is cut to increase elastic force. The upper surface 35, the side walls 34, and the lower surface 36 are formed integrally with each other, and a circular central opening 33 is defined by the upper surface 35, the side walls 34, and the lower surface 36.

Shoulder parts 38 are formed at boundaries between the upper surface 35 and the side walls 34 to protrude upward from the upper surface 35 in a step shape. First stopping protrusions 31 are formed on upper surfaces of the shoulder parts 38 to protrude upward in an "L" shape. Second stopping protrusions 32 are formed at vicinities of boundaries between the upper surface 35 and the shoulder parts 38 on the rear side of the upper surface 35 to protrude upward in an "L" shape.

The X-ray tube 20 is fitted with the above-configured central opening 33 of the tube guide 30, so that the X-ray tube 20 is elastically and fixedly supported, Referring back to FIG. 1, the high-voltage transformer structure 40, the high-voltage capacitors 50, and the high-voltage diodes 60, which are mentioned above, are located above the X-ray tube 20 which is fitted with the central opening 33 of the tube guide 30 to be fixedly supported.

Figure 3:
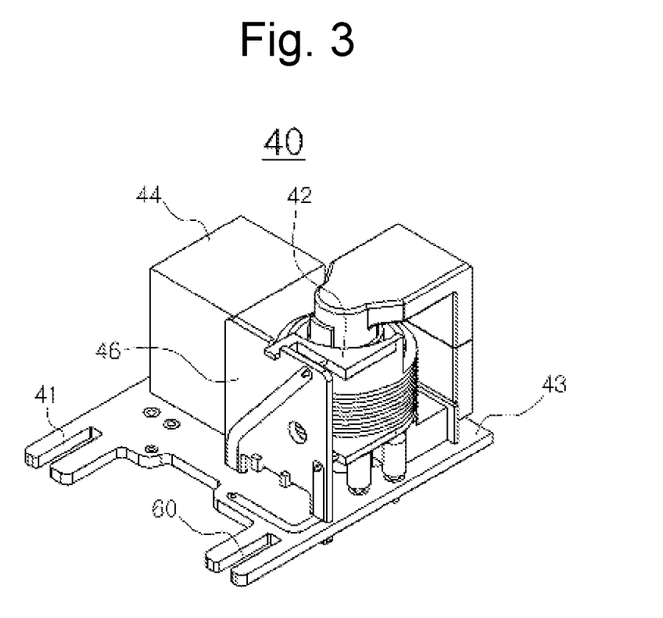
FIG. 3 is a perspective view illustrating a high-voltage transformer structure of FIG. 1.
Figure 4:
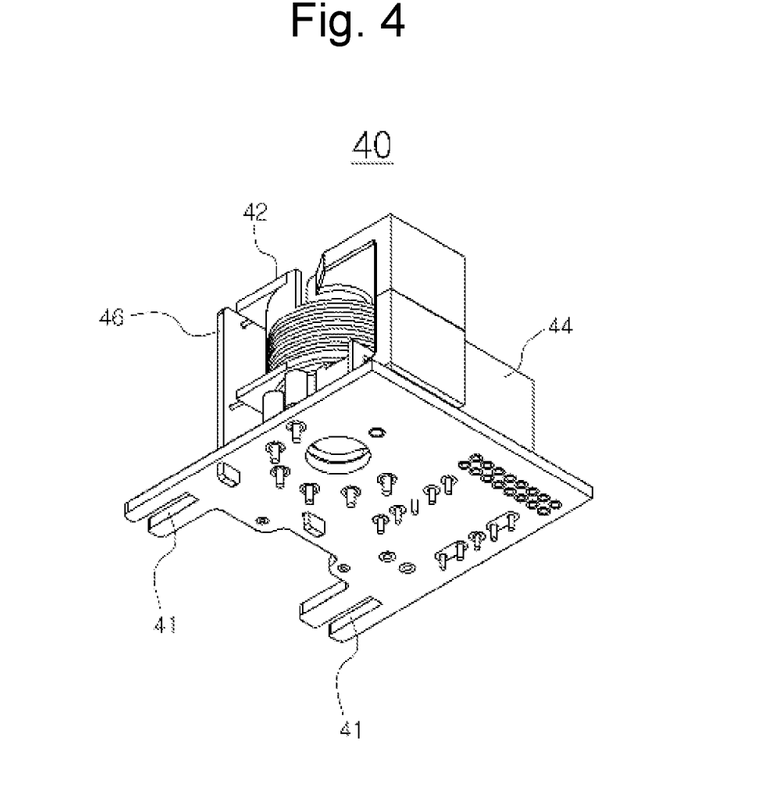
FIG. 4 is a bottom perspective view illustrating the high-voltage transformer structure of FIG. 1.

The high-voltage transformer structure 40 is illustrated in FIGS. 3 and 4.

Referring to FIGS. 3 and 4, the high-voltage transformer structure 40 includes a high-voltage transformer 42 and a filament transformer 44, which are fixedly arranged on a flat PCB substrate 43. In this case, a sub PCB 46 is uprightly arranged to be adjacent to the high-voltage transformer 42 on the PCB substrate 43. Stopping grooves 41 are formed through vicinities of opposite edges of the PCB substrate 43 at locations spaced apart from the high-voltage transformer 42 and the filament transformer 44. When the above-configured high-voltage transformer structure 40 is arranged on the tube guide 30, the first stopping protrusions 31 of the tube guide 30 are inserted into and fitted with the stopping grooves 41 formed in the PCB substrate 43, so that the high-voltage transformer structure 40 is fixedly supported on the tube guide 30.

Referring back to FIG. 1, in the high-voltage transformer structure 40 fixedly supported on the tube guide 30, a coil connector 45 is arranged on the uprightly arranged sub PCB 46. Accordingly, 16 connector pins 47 are arranged at upper portions and lower portions of an outer surface of the sub PCB 46. The coil connector 45 according to the present invention is enlarged to accommodate a relatively large current capacity due to an insufficient current capacity that the conventional high-voltage primary coil connector can accommodate.

Figure 5:
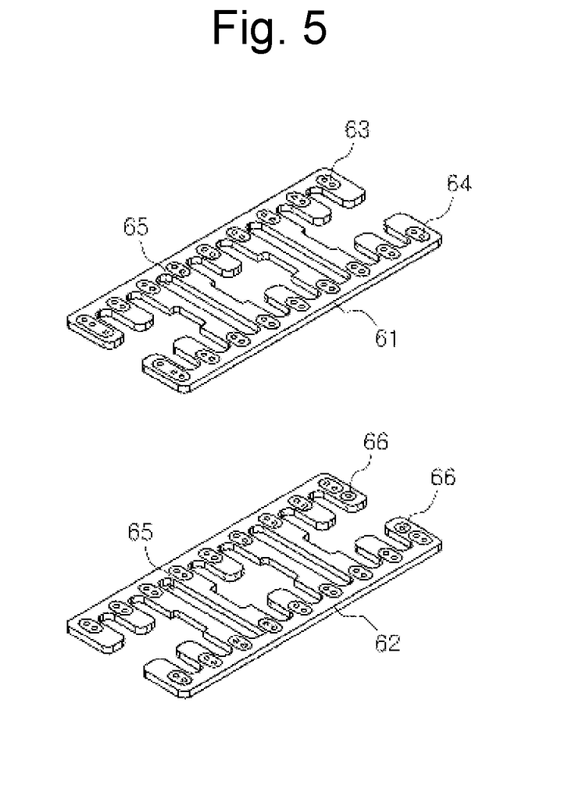
FIG. 5 is a view illustrating layout of substrates for fixedly arranging high-voltage capacitors and high-voltage diodes and a state in which the high-voltage diodes are arranged on the substrates.

FIG. 5 illustrates layouts of substrates for fixedly arranging the high-voltage capacitors 50 and the high-voltage diodes 60 and a state in which the high-voltage diodes are arranged on the substrates.

Referring to FIGS. 1 and 5, the plurality of high-voltage capacitors 50 for generating DC high voltage applied to the X-ray tube 20 are arranged between an upper substrate 61 and a lower substrate 62, and the plurality of high-voltage diodes 60 are arranged on an upper surface of the upper substrate 61 and a lower surface of the lower substrate 62.

According to the present invention, there is no filament so that power consumption may e greatly reduced. Further, to miniaturize a high voltage apparatus, the high-voltage capacitors 50 and the high-voltage diodes 60 are arranged in a space-intensive manner.

To this end, a plurality of mounting slots 65 are formed on the upper substrate 61 and the lower substrate 62 in accordance with the number of the high-voltage diodes 60 through cutting. The mounting slots 65 are spaced apart from each other at regular intervals. The high-voltage diodes 60 are arranged on the mounting slots 65. A high-voltage input site 63 is provided at one edge of the upper substrate 61, and a grounding site 64 is provided to be spaced apart from the high-voltage input site 63. A high-voltage output side 66 is provided at one edge of the lower substrate 62. The high-voltage capacitors 50 are arranged between the upper substrate 61 and the lower substrate on which the plurality of high-voltage diodes 60 are arranged on the upper surface and the lower surface thereof, respectively.

Figure 6:
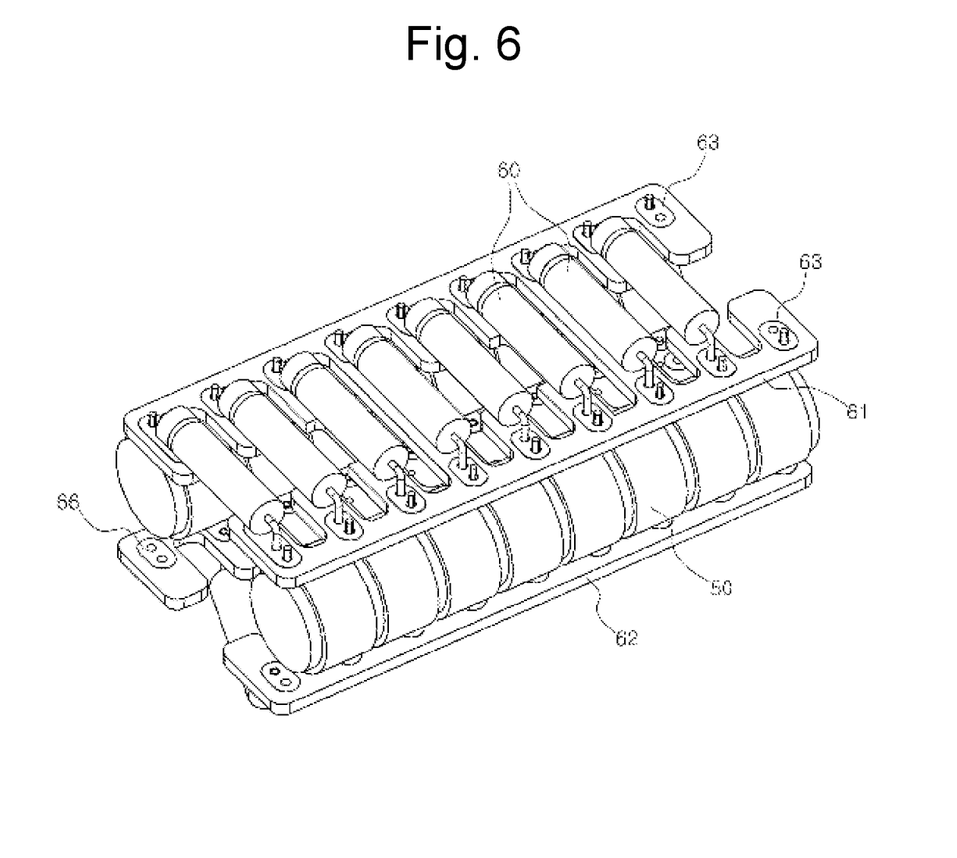
FIG. 6 is a view illustrating a state in which the high-voltage capacitors and the high-voltage diodes are finally arranged on the substrates of FIG. 5.

FIG. 6 is a view illustrating a state in which the high-voltage capacitors and the high-voltage diodes are finally arranged.

Referring to FIGS. 1 and 6, after the high-voltage capacitors 50 and the high-voltage diodes 60 are arranged in a space-intensive manner, in a state in which a portion of the lower substrate 62 is placed on the PCB substrate 43, and the other portion of the lower substrate 62 is placed on the X-ray tube 20, the second stopping protrusions 32 of the tube guide 30 are fastened to an edge of an upper surface of the lower substrate 52, so that a stack structure is fixedly supported.

Figure 7:
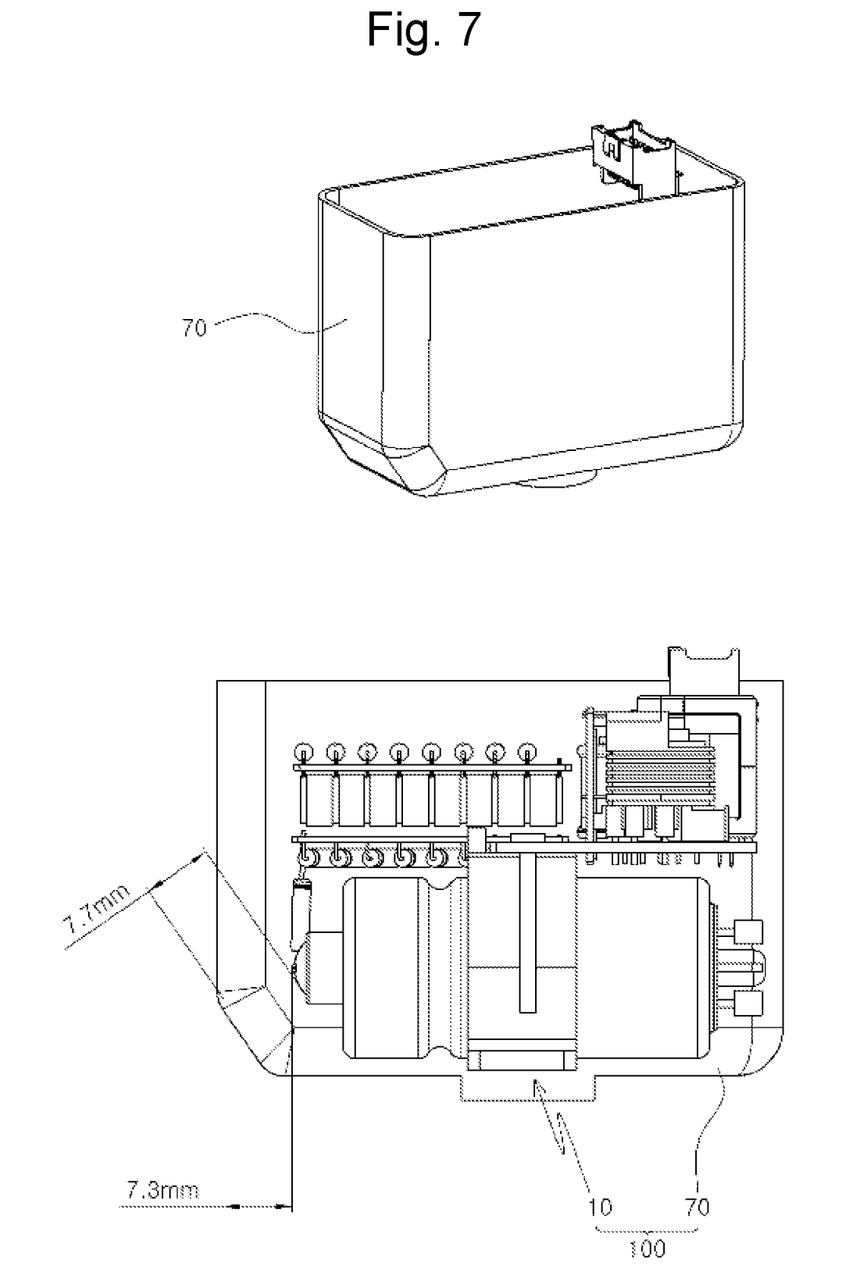
FIG. 7 is a perspective view illustrating an X-ray module assembly for a portable X-ray device according to the exemplary embodiment of the present invention.

FIG. 7 is a perspective view illustrating a case for embedding an X-ray module assembly for a portable X-ray device and an arrangement state thereof according to the exemplary embodiment of the present invention.

Referring to FIG. 7, the above-described X-ray module 10 for a portable X-ray device is embedded in a module case 70 having an open-topped box shape according to the present invention. In this case, bottom edges of the module case 70 are chamfered to make the portable X-ray device lighter than the conventional portable X-ray device. That is, the bottom edges of the module case 70 are chamfered such that an insulation distance between a high voltage side of the X-ray tube 20 and an inner side of the module case 70 is a minimum of 7 mm. The total weight of the dental X-ray photographing device according to the related art is 1,200 g, and the module assembly thereof including the case occupies 50% of the total weight. Thus, it is difficult to operate the product with one hand due to characteristics of the product, and thus, it is necessary to develop a lighter product. To solve the above technical problem, the bottom edges of the module case 70 are chambered.

Meanwhile, in a state in which the X-ray module 10 is arranged inside the module case 70, the X-ray module 10 is molded by using thermosetting resin, preferably, epoxy-based resin, more preferably, soft epoxy-based resin. In the related art, the X-ray module 10 is molded by using insulating oil or a silicon-based material to shield X-rays and insulate high voltage. However, there is a problem in that it is impossible to permanently use the insulating oil, and the silicon has an excellent insulating effect, but has bad insulating ability by a change in a temperature. In the present invention, thermosetting resin that has an excellent insulating effect and is resistant to thermal shock, preferably, epoxy-based resin, more preferably, soft epoxy-based resin are used together with a hardener, so that the molding material may be semi-permanently used, and an insulating effect is maintained even when the molding material is exposed to air for a long time. Further, an excellent insulating effect is maintained even with the change in a temperature. In addition, the X-ray photographing device may be miniaturized and lightened, so that the X-ray photographing device may be conveniently stored, manipulated, and moved.

The above description is a simple exemplification of the technical spirit of the present disclosure, and the present disclosure may be variously corrected and modified by those skilled in the art to which the present disclosure pertains without departing from the essential features of the present disclosure. Therefore, the disclosed embodiments of the present invention do not limit the technical spirit of the present invention but are illustrative, and the scope of the present invention is not limited by the embodiments of the present disclosure. The scope of the present invention should be construed by the claims, and it will be understood that all the technical spirits within the same scope or the equivalent range are fall within the scope of the present invention.

What is claimed is:

1. An X-ray module assembly for a portable X-ray device, the X-ray module assembly comprising:
    an X-ray module comprising an X-ray tube, a high-voltage transformer structure, a plurality of high-voltage capacitors, and a plurality of high-voltage diodes; and
    a module case having an open-topped box shape, for embedding the X-ray module therein,
    wherein the X-ray tube is fixedly supported by a tube guide, the plurality of high-voltage capacitors are arranged between an upper substrate and a lower substrate, and the plurality of high-voltage diodes are arranged on an upper surface of the upper substrate and a lower surface of the lower substrate.

2. The X-ray module assembly of claim 1, wherein the X-ray tube is a carbon nanotube (CNT) or a filament-type tube.

3. The X-ray module assembly of claim 1, wherein the tube guide comprises a flat upper surface, side walls extending downward from opposite sides of the upper surface, and a lower surface connecting lower portions of the side walls to each other,
    wherein the upper surface, the side walls, and the lower surface are formed integrally with each other, and a circular central opening for accommodating the X-ray tube is defined by the upper surface, the side walls, and the lower surface.

4. The X-ray module assembly of claim 3, wherein shoulder parts protrude upward from boundaries between the flat upper surface and each of the side walls in a step shape with respect to the flat upper surface, first stopping protrusions protrude upward from upper surfaces of each of the shoulder parts, and second stopping protrusions protrude upward from vicinities of boundaries between the flat upper surface and the shoulder parts on a rear side of the flat upper surface.

5. The X-ray module assembly of claim 4, wherein the high-voltage transformer structure comprises a high-voltage transformer and a filament transformer which are fixedly arranged on a PCB substrate,
    wherein a sub PCB is arranged upright on the PCB substrate at a location that is adjacent to the high-voltage transformer, stopping grooves are formed through vicinities of opposite edges of the PCB substrate at locations spaced apart from the high-voltage transformer and the filament transformer, and a coil connector is arranged on the sub PCB, and
    wherein the high-voltage transformer structure is fixedly supported on the tube guide by inserting and fitting the first stopping protrusions of the tube guide into and with the stopping grooves, when the high-voltage transformer structure is arranged above the tube guide.

6. The X-ray module assembly of claim 4, wherein a plurality of mounting slots are formed on the upper substrate and the lower substrate at regular intervals corresponding to a number of the plurality of high-voltage diodes to be mounted, the plurality of high-voltage diodes are arranged above the plurality of the mounting slots, and the tube guide is fixedly supported by coupling and attaching the second stopping protrusions of the tube guide to edges of an upper surface of the lower substrate.

7. The X-ray module assembly of claim 1, wherein when a voltage is 100 kV and soft epoxy is filled, bottom edges of the module case are chamfered for lightweight such that an insulation distance between a high-voltage side of the X-ray tube and an inner side of the module case is at least 7 to 8 mm.

8. The X-ray module assembly of claim 2, wherein when a voltage is 100 kV and soft epoxy is filled, bottom edges of the module case are chamfered for lightweight such that an insulation distance between a high-voltage side of the X-ray tube and an inner side of the module case is at least 7 to 8 mm.

9. The X-ray module assembly of claim 3, wherein when a voltage is 100 kV and soft epoxy is filled, bottom edges of the module case are chamfered for lightweight such that an insulation distance between a high-voltage side of the X-ray tube and an inner side of the module case is at least 7 to 8 mm.

10. The X-ray module assembly of claim 4, wherein when a voltage is 100 kV and soft epoxy is filled, bottom edges of the module case are chamfered for lightweight such that an insulation distance between a high-voltage side of the X-ray tube and an inner side of the module case is at least 7 to 8 mm.

11. The X-ray module assembly of claim 5, wherein when a voltage is 100 kV and soft epoxy is filled, bottom edges of the module case are chamfered for lightweight such that an insulation distance between a high-voltage side of the X-ray tube and an inner side of the module case is at least 7 to 8 mm.

12. The X-ray module assembly of claim 6, wherein when a voltage is 100 kV and soft epoxy is filled, bottom edges of the module case are chamfered for lightweight such that an insulation distance between a high-voltage side of the X-ray tube and an inner side of the module case is at least 7 to 8 mm.

* * * * *